(12) United States Patent
Kwak (10) Patent No.: US 8,076,674 B2
(45) Date of Patent: Dec. 13, 2011

(54) DISPLAY DEVICE

(75) Inventor: Won-Kyu Kwak, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 126 days.

(21) Appl. No.: 12/247,171

(22) Filed: Oct. 7, 2008

(65) Prior Publication Data

US 2009/0039355 A1     Feb. 12, 2009

Related U.S. Application Data

(62) Division of application No. 11/129,016, filed on May 13, 2005.

(30) Foreign Application Priority Data

May 24, 2004 (KR) .................. 10-2004-0036855

(51) Int. Cl.
    *H01L 27/15*     (2006.01)
    *H01L 31/12*     (2006.01)
    *H01L 33/00*     (2010.01)

(52) U.S. Cl. ............... 257/79; 257/88; 257/E33.001

(58) Field of Classification Search ............. 257/79, 257/88, 89, E33.001, E31.127
See application file for complete search history.

(56) References Cited

U.S. PATENT DOCUMENTS

| | | | |
|---|---|---|---|
| 5,822,026 A | 10/1998 | Matsuo | |
| 5,952,789 A | 9/1999 | Stewart et al. | |
| 5,966,189 A | 10/1999 | Matsuo | |
| 6,404,410 B1 | 6/2002 | Shirae | |
| 6,421,033 B1 | 7/2002 | Williams et al. | |
| 6,583,775 B1 | 6/2003 | Sekiya et al. | |
| 6,618,031 B1 | 9/2003 | Bohn, Jr. et al. | |
| 6,686,985 B1 | 2/2004 | Tanaka et al. | |
| 6,768,482 B2 | 7/2004 | Asano et al. | |
| 6,771,028 B1 | 8/2004 | Winters | |
| 6,919,681 B2 | 7/2005 | Cok et al. | |

(Continued)

FOREIGN PATENT DOCUMENTS

CN     1143232 A     2/1997

(Continued)

OTHER PUBLICATIONS

U.S. Office action dated Oct. 3, 2008, for related U.S. Appl. No. 11/239,726, indicating relevance of listed U.S. references in this IDS.

(Continued)

*Primary Examiner* — Hoai v Pham
(74) *Attorney, Agent, or Firm* — Christie, Parker & Hale, LLP (57) ABSTRACT

A current pixel circuit of a display device includes a switching transistor which may be turned on in response to the current selection signal to transfer a data signal, a driving transistor for outputting a current corresponding to the data signal, and first and second transistors being turned on in response to the previous selection signal. In the display device, the gate electrodes of the switching transistor of a previous pixel and the first and second transistors of the current pixel are coupled to one scan line for transferring the previous selection signal. Accordingly, the transistors are arranged in the order of the switching transistor of the previous pixel and the first and second transistors of the current pixel on the scan line at an area between two adjacent data lines.

5 Claims, 6 Drawing Sheets

U.S. PATENT DOCUMENTS

| | | | |
|---|---|---|---|
| 6,933,756 | B2 | 8/2005 | Miyazawa |
| 7,336,251 | B2 | 2/2008 | Osada |
| 7,394,513 | B2 | 7/2008 | Andou et al. |
| 7,561,124 | B2 | 7/2009 | Kwak et al. |
| 7,880,698 | B2 | 2/2011 | Park et al. |
| 2002/0000576 | A1 | 1/2002 | Inukai |
| 2002/0021293 | A1 | 2/2002 | Tam |
| 2003/0062524 | A1 | 4/2003 | Kimura |
| 2003/0094612 | A1 | 5/2003 | Yamazaki et al. |
| 2003/0117348 | A1 | 6/2003 | Knapp et al. |
| 2003/0132896 | A1 | 7/2003 | Matsueda |
| 2004/0100427 | A1 | 5/2004 | Miyazawa |
| 2004/0113922 | A1 | 6/2004 | Choe et al. |
| 2004/0183758 | A1 | 9/2004 | Chen et al. |
| 2004/0217694 | A1 | 11/2004 | Cok et al. |
| 2004/0239658 | A1 | 12/2004 | Koyama et al. |
| 2004/0263499 | A1 | 12/2004 | Tanada et al. |
| 2005/0024305 | A1 | 2/2005 | Park |
| 2005/0052365 | A1 | 3/2005 | Jang |
| 2005/0068271 | A1 | 3/2005 | Lo |
| 2005/0083271 | A1* | 4/2005 | Suh et al. .................. 345/76 |
| 2005/0093791 | A1 | 5/2005 | Lo |
| 2005/0104817 | A1 | 5/2005 | Kwak |
| 2005/0190126 | A1 | 9/2005 | Kimura et al. |
| 2006/0038752 | A1 | 2/2006 | Winters |
| 2006/0061531 | A1 | 3/2006 | Park et al. |
| 2006/0076550 | A1 | 4/2006 | Kwak et al. |
| 2006/0132668 | A1 | 6/2006 | Park et al. |

FOREIGN PATENT DOCUMENTS

| | | |
|---|---|---|
| CN | 1361510 | 7/2002 |
| CN | 1376014 A | 10/2002 |
| CN | 1410962 A | 4/2003 |
| CN | 1444197 A | 9/2003 |
| CN | 1455914 A | 11/2003 |
| CN | 1460240 A | 12/2003 |
| CN | 1479272 A | 3/2004 |
| CN | 1497522 A | 5/2004 |
| CN | 1530910 A | 9/2004 |
| CN | 1551383 A | 12/2004 |
| EP | 1 215 651 A2 | 6/2002 |
| JP | 9-138659 | 5/1997 |
| JP | 2001-318628 | 11/2001 |
| JP | 2002-23697 | 1/2002 |
| JP | 2002-175029 | 6/2002 |
| JP | 2002-198174 | 7/2002 |
| JP | 2002-215093 | 7/2002 |
| JP | 2002-215096 | 7/2002 |
| JP | 2002-221917 | 8/2002 |
| JP | 2003-043999 | 2/2003 |
| JP | 2003-108032 | 4/2003 |
| JP | 2003-122306 | 4/2003 |
| JP | 2003-216100 | 7/2003 |
| JP | 2004-133240 | 4/2004 |
| JP | 2004-279548 | 10/2004 |
| JP | 2005-031630 | 2/2005 |
| KR | 2000-0039659 | 7/2000 |
| KR | 2001-0050783 | 6/2001 |
| KR | 2002-0025842 | 4/2002 |
| KR | 2002-0040613 | 5/2002 |
| KR | 2003-0027858 | 4/2003 |
| KR | 2003-0086166 | 11/2003 |
| KR | 10-2004-0029242 | 4/2004 |
| WO | WO 03/044762 A1 | 5/2003 |
| WO | WO 03/071511 A2 | 8/2003 |

OTHER PUBLICATIONS

U.S. Office action dated Nov. 13, 2008, for related U.S. Appl. No. 11/129,016, indicating relevance of listed U.S. references in this IDS.

U.S. Notice of Allowance dated Nov. 4, 2008, for related U.S. Appl. No. 11/274,042, indicating relevance of listed U.S. references in this IDS.

Patent Abstracts of Japan, Publication No. 09-138659, dated May 27, 1997, in the name of Chan-Long Shieh et al.

Patent Abstracts of Japan, Publication No. 2002-175029, dated Jun. 21, 2002, in the name of Katsuya Anzai et al.

Patent Abstracts of Japan, Publication No. 2002-198174 dated Jul. 12, 2002, in the name of Yuichi Ikezu et al.

Patent Abstracts of Japan, Publication No. 2002-221917 dated Aug. 9, 2002, in the name of Shin Asano et al.

Patent Abstracts of Japan, Publication No. 2003-043999, dated Feb. 14, 2003, in the name of Suzuki.

Patent Abstracts of Japan, Publication No. 2003-108032, dated Apr. 11, 2003, in the name of Katsuya Anzai.

Patent Abstracts of Japan, Publication No. 2003-122306, dated Apr. 25, 2003, in the name of Akira Yumoto.

Patent Abstracts of Japan, Publication No. 2004-133240, dated Apr. 30, 2004, in the name of Shin Asano et al.

Korean Patent Abstracts, Publication No. 1020020025842 A, dated Apr. 4, 2002, in the name of Katsuya Anzai et al.

Korean Patent Abstracts, Publication No. 1020020040613 A, dated May 30, 2002, in the name of Mitsuru Asano.

Korean Patent Abstracts, Publication No. 1020030027858 A dated Apr. 7, 2003, in the name of Katsuya Anzai.

U.S. Office action dated Mar. 4, 2010, for related U.S. Appl. No. 11/129,016, noting listed reference in this IDS.

Chinese Patent Publication dated Oct. 7, 2009, for corresponding Chinese application 200510129187.6, noting listed references in this IDS, as well as CN 1376014 and CN 1530910, both previously filed in an IDS dated Dec. 20, 2008.

U.S. Office action dated Jan. 15, 2010, for related U.S. Appl. No. 11/239,726, noting listed reference in this IDS.

U.S. Office action dated Mar. 23, 2009, for related U.S. Appl. No. 11/239,726, noting listed reference in this IDS, namely, U.S. Patent 6,771,028.

U.S. Notice of Allowance dated Apr. 21, 2009, for related U.S. Appl. No. 11/274,057, noting listed references in this IDS, namely, U.S. Patent 5,952,789 and U.S. Publication 2006/0038752.

U.S. Office action dated May 8, 2009, for U.S. Appl. No. 11/129,016, noting listed references in this IDS.

S.M. Choi et al., *A Self-compensated Voltage Programming Pixel Structure for Active-Matrix Organic Light Emitting Diodes*, IDW 2003, Proceedings of the 10th Int'l Display Workshops, pp. 535-538, XP 008057381.

Japanese Office action dated Apr. 7, 2009, for Japanese application 2005-306198, noting Japanese references listed in this IDS.

U.S. Office action dated Sep. 28, 2009, for related U.S. Appl. No. 11/129,016, noting listed U.S. Publication references in this IDS.

Patent Abstracts of Japan, Publication No. 2001-318628, dated Nov. 16, 2001, in the name of Shunpei Yamazaki et al.

Patent Abstracts of Japan, Publication No. 2002-023697, dated Jan. 23, 2002, in the name of Kazutaka Inukai.

Patent Abstracts of Japan, Publication No. 2002-215093 dated Jul. 31, 2002, in the name of Akira Yumoto et al.

Patent Abstracts of Japan, Publication No. 2002-215096, dated Jul. 31, 2002, in the name of Oh-Kyong Kwon.

Patent Abstracts of Japan, Publication No. 2003-216100, dated Jul. 30, 2003, in the name of Hiroshi Takahara.

Korean Patent Abstracts, Publication No. 1020000039659 A; Date of Publication: Jul. 5, 2000; in the name of U Yeong Kim et al.

Korean Patent Abstracts, Publication No. 1020010050783 A; Date of Publication: Jun. 25, 2001; in the name of Tsutomu Yamada.

Korean Patent Abstracts, Publication No. 1020030086166 A; Date of Publication: Nov. 7, 2003; in the name of Gi Seong Chae et al.

Korean Patent Abstracts, Publication No. 1020040029242 A; Date of Publication: Apr. 6, 2004; in the name of Jong Cheol Chae et al.

U.S. Office action dated Jul. 19, 2010 in U.S. Appl. No. 11/129,016, noting listed reference in this IDS.

U.S. Office action dated Mar. 30, 2011 in U.S. Appl. No. 11/129,016.

U.S. Notice of Allowance dated Apr. 11, 2011 in cross reference U.S. Appl. No. 11/239,726.

U.S. Notice of Allowance dated Jul. 21, 2011, for cross reference U.S. Appl. No. 11/239,726, 19 pages.

* cited by examiner

DISPLAY DEVICE

CROSS REFERENCE TO RELATED APPLICATION

This application is a divisional of U.S. application Ser. No. 11/129,016, filed on May 13, 2005 which claims priority to and the benefit of Korean Patent Application No. 10-2004-0036855 filed on May 24, 2004 in the Korean Intellectual Property Office, the entire content of which is incorporated herein by reference.

BACKGROUND OF THE INVENTION (a) Field of the Invention

The present invention relates to a displaying device. More specifically, the present invention relates to an organic electro-luminescence (herein also referred to as EL) light-emitting display using the electro-luminescence of an organic material.

(b) Description of the Related Art

The organic EL light-emitting display, which is a device for electrically exciting an organic fluorescent material to emit a light, drives n×m organic light-emitting elements arranged in a matrix to represent an image.

The organic light-emitting element, also called "organic light-emitting diode (herein also referred to as OLED)" because of its diode characteristic, has a structure of an Indium Tin Oxide (herein also referred to as ITO) anode, an organic thin film, and a cathode electrode (e.g., metal) layer. The organic thin film has a multi-layer structure that includes a light-emitting layer (herein also referred to as EML), an electron transport layer (herein also referred to as ETL), and a hole transport layer (herein also referred to as HTL) to keep electrons and holes in good balance and enhance the light-emitting efficiency. The organic thin film may also include an electron injecting layer (herein also referred to as EIL) and a hole injecting layer (herein also referred to as HIL). The n×m organic light-emitting elements are arranged in a matrix to form an organic EL display panel.

There are two driving methods for the organic light-emitting elements: the passive matrix method and the active matrix method using thin film transistors (TFTs.) The passive matrix method forms anode and cathode lines arranged orthogonal to (or to cross over) each other and select the anode and cathode lines to drive the organic light-emitting elements. The active matrix method sequentially turns on a plurality of TFTs coupled to data lines and scan lines to drive the organic light-emitting elements.

Hereinafter, a pixel circuit of a general active matrix organic EL display device will be described.

Figure 1:
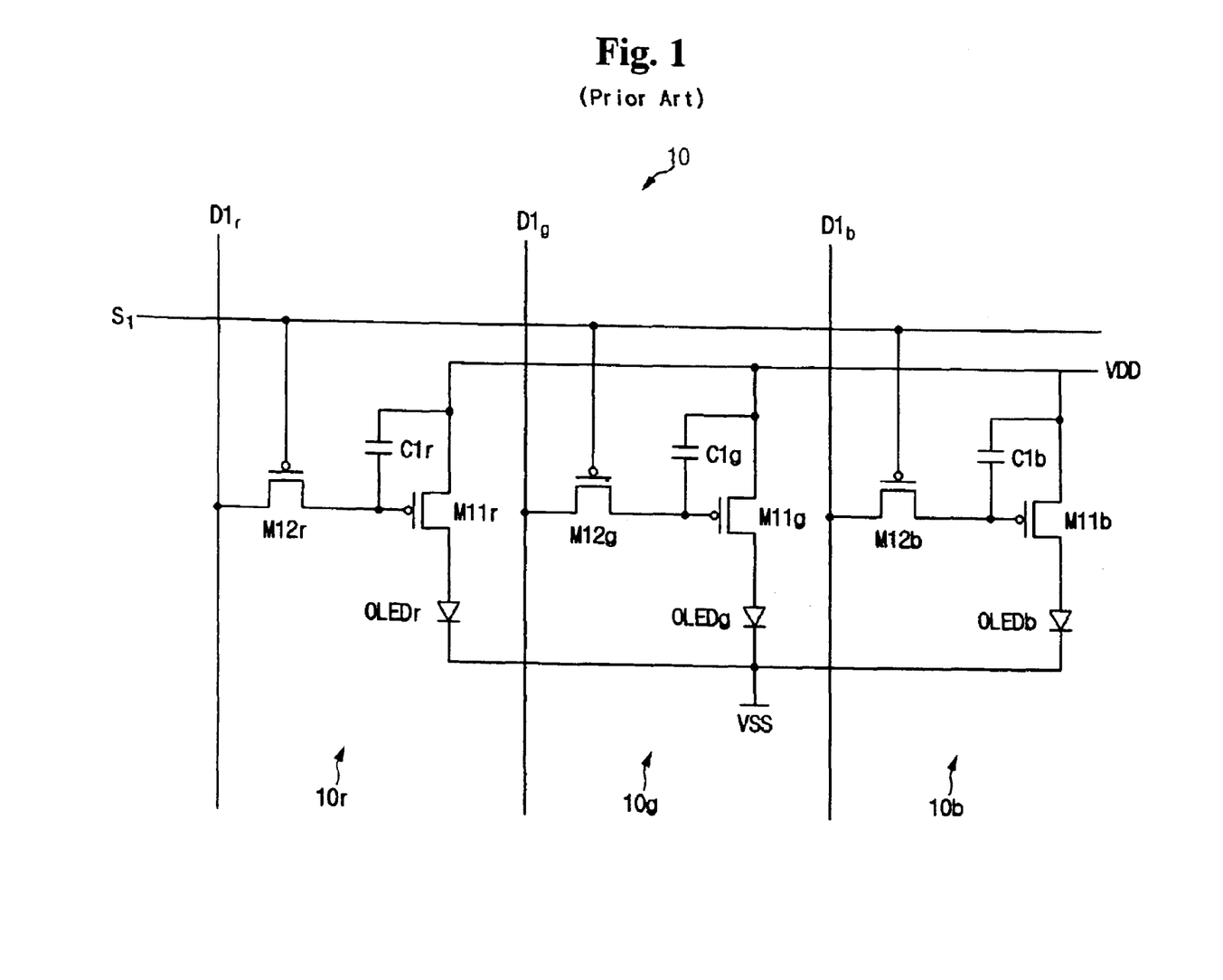
FIG. 1 is a circuit diagram of a pixel circuit of a light-emitting display panel.

FIG. 1 is an equivalent circuit diagram of one of n×m pixels, i.e., a pixel on a first row and a first column of the n×m pixels.

Referring to FIG. 1, a pixel 10 includes three sub-pixels 10r, 10g and 10b, which have organic light-emitting elements OLEDr, OLEDg and OLEDb to emit red (R), green (G) and blue (B) lights, respectively. In a stripe arrangement structure, the sub-pixels 10r, 10g and 10b are coupled to independent data lines D1r, D1g and D1b, and a common scan line S1.

The red sub-pixel 10r includes two transistors M11r and M12r and a capacitor C1r for driving the organic light-emitting element OLEDr. Likewise, the green sub-pixel 10g includes two transistors M11g and M12g and a capacitor C1g for driving the organic light-emitting element OLEDg, and the blue sub-pixel 10b includes two transistors M11b and M12b and a capacitor C1b for driving the organic light-emitting element OLEDb. The connections and operations of the sub-pixels 10r, 10g and 10b are substantially the same. As such, the connection and operation of only the sub-pixel 10r will be described below by way of an example.

The driving transistor M11r is coupled between a power supply voltage VDD and the anode of the organic light-emitting element OLEDr to transfer a current for light emission to the organic light-emitting element OLEDr. A cathode of the organic light-emitting element OLEDr is coupled to a voltage VSS, which is lower than the power supply voltage VDD. The amount of current of the driving transistor M11r is controlled by a data voltage applied through a switching transistor M12r. Here, a capacitor C1r is coupled between a source and a gate of the transistor M11r to sustain (or maintain) the applied voltage for a predetermined time period. The transistor M12r has a gate coupled to a scan line S1 for transferring an on/off selection signal (or select signal), and a source coupled to a data line D1r for transferring a data voltage corresponding to the red sub-pixel 10r.

In operation, when the switching transistor M12r is turned on in response to the selection signal applied to its gate, a data voltage $V_{DATA}$ from the data line D1r is applied to the gate of the transistor M11r. Then, a current $I_{OLED}$ flows to (and/or through) the transistor M11r according to a voltage $V_{GS}$ charged between the gate and the source by the capacitor C1r. The organic light-emitting element OLEDr then emits a light according to the current $I_{OLED}$ Here, the current $I_{OLED}$ flowing to the organic light-emitting element OLEDr is given by the following Equation 1.

$$I_{OLED} = \frac{\beta}{2}(V_{GS} - V_{TH})^2 = \frac{\beta}{2}(V_{DD} - V_{DATA} - |V_{TH}|)^2 \quad \text{[Equation 1]}$$

where $V_{TH}$ is the threshold voltage of the transistor M11r; and β is a constant.

As can be seen from the Equation 1, in the pixel circuit of FIG. 1, a current corresponding to the data voltage is supplied to the organic light-emitting element OLEDr, causing the organic light-emitting element OLEDr to emit a light with a brightness corresponding to it. The data voltage applied has a multilevel value in a defined range so as to represent a predetermined brightness gradation.

In the organic EL display device, one pixel 10 includes three sub-pixels 10r, 10g and 10b, each of which has a driving transistor (M11r, M11g, or M11b) for driving an organic light-emitting element, a switching transistor (M12r, M12g, or M12b), and a capacitor (C1r, C1g, or C1b). Each sub-pixel also has a data line (D1r, D1g, or D1b) for transferring a data signal, and a power line for transferring the power supply voltage VDD.

Therefore, such a construction requires a large number of elements such as transistors and capacitors formed in one pixel and hence a large number of interconnections to transfer voltages or signals, so there is a considerable difficulty in arranging all the component elements in one pixel area.

SUMMARY OF THE INVENTION

It is an aspect of the present invention to provide a light-emitting display panel and a light-emitting display capable of efficiently arranging component elements of a pixel circuit in a given pixel area.

In one embodiment of the present invention, there is provided a display device that includes: first and second scan lines extending in a first direction, and transferring first and second selection signals, respectively; first and second data lines insulatively intersecting the first and second scan lines, extending in a second direction, and transferring first and second data signals, respectively; and a pixel circuit formed in a pixel area defined by the first and second scan lines and the first and second data lines. The pixel circuit includes: a first transistor having a control electrode coupled to the first scan line, and being turned on in response to the first selection signal to transfer the first data signal; a second transistor for outputting a current corresponding to the first data signal; and a third transistor having a control electrode coupled to the second scan line, and being turned on in response to the second selection signal. The first transistor is arranged adjacent to the first data line. The third transistor is arranged adjacent to the second data line. The first and third transistors are arranged on a diagonal line of the pixel area having the pixel circuit formed therein.

The pixel circuit may further include a fourth transistor having a control electrode coupled to the second scan line, and being turned on in response to the second selection signal; and a power electrode line insulatively intersecting the first and second scan lines, extending in the second direction, and being arranged between the first and second data lines.

The third transistor may be arranged between the power electrode line and the second data line. The second transistor may be arranged between the fourth transistor and the power electrode line.

The pixel circuit may further include: first, second and third light-emitting elements for emitting a light corresponding to a current output from the second transistor; and fifth, sixth and seventh transistors coupled between the second transistor and the first, second and third light-emitting elements, respectively, to control a light emission of the first, second and third light-emitting elements.

In another embodiment of the present invention, there is provided a light-emitting display panel that includes: a scan line having an extending area extending lengthwise in a first direction; first, second and third semiconductor layer areas insulatively intersecting the extending area of the scan line; and a data electrode extending in a second direction, and being coupled to the one end of the first semiconductor layer area through a contact hole. The second semiconductor layer area is arranged between the first semiconductor layer area and the third semiconductor layer area.

Each of the first, second and third semiconductor layer areas may intersect the scan line at least twice. The first semiconductor layer area may be formed in an approximately "U" shape. The second and third semiconductor layer areas may be formed in an approximately "n" shape.

One embodiment of the present invention includes a light-emitting display panel that has a plurality of pixel circuits. Each pixel circuit includes a plurality of scan lines including a first scan line having at least a part extending lengthwise in a first direction to transfer a first selection signal and a plurality of data lines extending in a second direction to transfer a data signal. A first pixel circuit and a second pixel circuit of the pixel circuits are coupled to the scan lines and the data lines, respectively. A first scan line of the scan lines is arranged between first and second pixel areas having the first and second pixel circuits formed therein. The first pixel circuit includes a first transistor that is turned on in response to the first selection signal. The second pixel circuit includes second and third transistors which are turned on in response to the first selection signal. The second transistor is arranged between the first transistor and the third transistor. The channel areas of the first, second and third transistors are arranged adjacent to one another in a parallel configuration.

The channel areas of the first, second and third transistors may be arranged adjacent to the part of the first scan line extending lengthwise in the first direction.

The first transistor may have a first electrode coupled to the data line and is turned on in response to the first selection signal to transfer the data signal.

In still another embodiment of the present invention, there is provided a light-emitting display that includes a plurality of scan lines including first and second scan lines extending in a first direction and for transferring first and second selection signals, a plurality of data lines insulatively intersecting the scan lines, extending in a second direction, and for transferring a data signal, a power electrode line, and a plurality of pixel circuits each coupled to the scan lines and the data lines. A pixel circuit of the pixel circuit includes: a first transistor having a control electrode coupled to the first scan line, and being turned on in response to the first selection signal to transfer the data signal; a second transistor having a control electrode coupled to the second scan line, and another transistor electrode coupled to the power electrode line; a third transistor having a first transistor electrode coupled to the power electrode line, and for outputting a current corresponding to a voltage difference between a control electrode of the third transistor and the power electrode line; a fourth transistor having a control electrode coupled to the second scan line, and being turned on in response to the second selection signal to diode-connect the third transistor; first, second and third light-emitting elements for emitting a light corresponding to the current output from the third transistor; and first, second and third light-emitting transistors coupled between a second transistor electrode of the third transistor and the first, second and third light-emitting elements, respectively. The first transistor is arranged adjacent to a first data line of the data lines. The second transistor is arranged adjacent to a second data line of the data line that is neighboring the first data line. The first and second transistors are arranged on a diagonal line in a pixel area having the pixel circuit formed therein.

The power electrode line may extend in the second direction and may be arranged between the first data line and the second data line.

The fourth transistor may be arranged between the first data line and the power electrode line, and the second transistor may be arranged between the second data line and the power electrode line.

The power electrode line may extend through an area between the second and third light-emitting elements.

BRIEF DESCRIPTION OF THE DRAWINGS

The accompanying drawings, together with the specification, illustrate exemplary embodiment(s) of the present invention, and, together with the description, serve to explain the principles of the present invention.

DETAILED DESCRIPTION

In the following detailed description, exemplary embodiment(s) of the present invention are shown and described, by way of illustration. As those skilled in the art would recognize, the described exemplary embodiment(s) may be modified in various ways, all without departing from the spirit or scope of the present invention. Accordingly, the drawings and description are to be regarded as illustrative in nature, and not restrictive.

There may be parts shown in the drawings, or parts not shown in the drawings, that are not discussed in the specification as they are not essential to a complete understanding of the invention. Like reference numerals designate like elements. When it is stated that a first component is coupled to a second component, the first and second components may be coupled directly to each other or a third component may be positioned between the first component and the second component. Also, a part such as a layer, a film, an area, or a plate is on another part may refer to a case where the part lies "right on" the another part, or a case where there is a third part between the part and the another part. The term "current scan line" as used herein refers to a scan line to transfer the current selection signal. The term "previous scan line" as used herein refers to a scan line that transferred a selection signal prior to the current selection signal. The term "current pixel" as used herein refers to a pixel that emits a light based on the selection signal of the current scan line. The term "previous pixel" as used herein refers to a pixel that emits a light based on the selection signal of the previous scan line. The term "next pixel" as used herein refers to a pixel that emits a light based on the selection signal of the next scan line.

Figure 2:
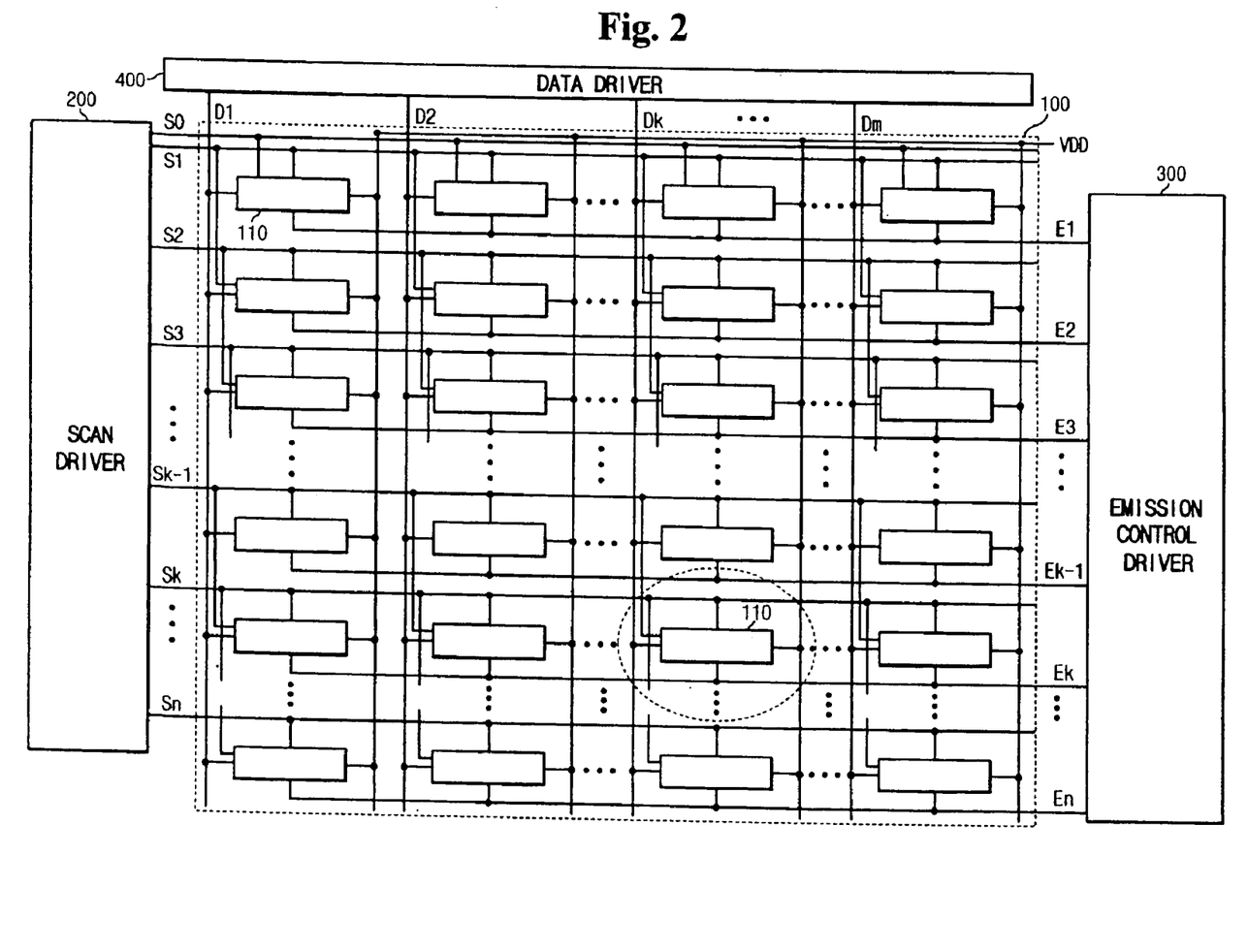
FIG. 2 is a schematic plan view of an organic EL display according to an exemplary embodiment of the present invention.

FIG. 2 is a schematic of an organic EL display according to an exemplary embodiment of the present invention.

The organic EL display according to the exemplary embodiment of the present invention includes, as shown in FIG. 2, a display panel 100, a scan driver 200, a light emission controller 300, and a data driver 400. The display panel 100 includes a plurality of scan lines S0, S1, . . . , Sk, . . . , and Sn, a plurality of light emission control lines E1, . . . , Ek, . . . , and En, a plurality of data lines D1, . . . , Dk, . . . , and Dm, a plurality of power lines for providing the power supply voltage VDD arranged in columns, and a plurality of pixels 110. Each of the pixels 110 is formed in a pixel area defined by two adjacent scan lines Sk−1 and Sk and two adjacent data lines Dk−1 and Dk. Each pixel 110 is driven by signals transferred (or transmitted) from the current scan line Sk, the previous scan line Sk−1, the light emission control line Ek, and the data line Dk. Each of the light emission control lines E1 to En respectively includes three types of light emission control lines E1r to Enr, E1g to Eng, and E1b to Enb (not shown in FIG. 2).

The scan driver 200 transfers a selection signal for selecting a corresponding line to the scan lines S0 to Sn in sequence so as to apply a data signal to the pixels of the corresponding line. The light emission controller 300 transfers a light emission control signal for controlling the light emission of the organic light-emitting elements OLEDr, OLEDg and OLEDb (not shown in FIG. 2) to the light emission control lines E1 to En in sequence. The data driver 400 sequentially applies to the data lines D1 to Dm the data signal corresponding to the pixels of the selected scan lines to which the selection signals are applied when the selection signals are sequentially applied.

The scan driver 200, the light emission controller 300, and the data driver 400 are coupled to a substrate in which the display panel 100 is formed. Alternatively, the scan driver 200, the light emission controller 300, and/or the data driver 400 can be mounted directly on a glass substrate of the display panel 100, or substituted by a driver circuitry including the same layers as scan lines, data lines and transistors formed in the substrate of the display panel 100. Alternatively, the scan driver 200, the light emission controller 300, and/or the data driver 400 can be mounted in the form of a chip on a tape carrier package (herein referred to as TCP), a flexible printed circuit (herein referred to as FPC), or a tape automatic bounding (herein also referred to as TAB) soldered and/or coupled to the substrate of the display panel 100.

Also, in the exemplary embodiment of the present invention, one field can be divided into three sub-fields on which red, green and blue data are written to emit a light or lights, respectively. For this purpose, the scan driver 200 transfers a selection signal for every sub-field to the scan lines S0 to Sn in sequence, and the light emission controller 300 applies a light emission control signal to the light emission control lines E1 to En, so the organic light-emitting element of each color can emit a light on one sub-field. The data driver 400 applies a data signal corresponding to each of the red, green and blue organic light-emitting elements for the three sub-fields to the data lines D1 to Dm.

An operation of the organic EL display according to the exemplary embodiment of the present invention will be described in detail with reference to FIG. 3.

Figure 3:
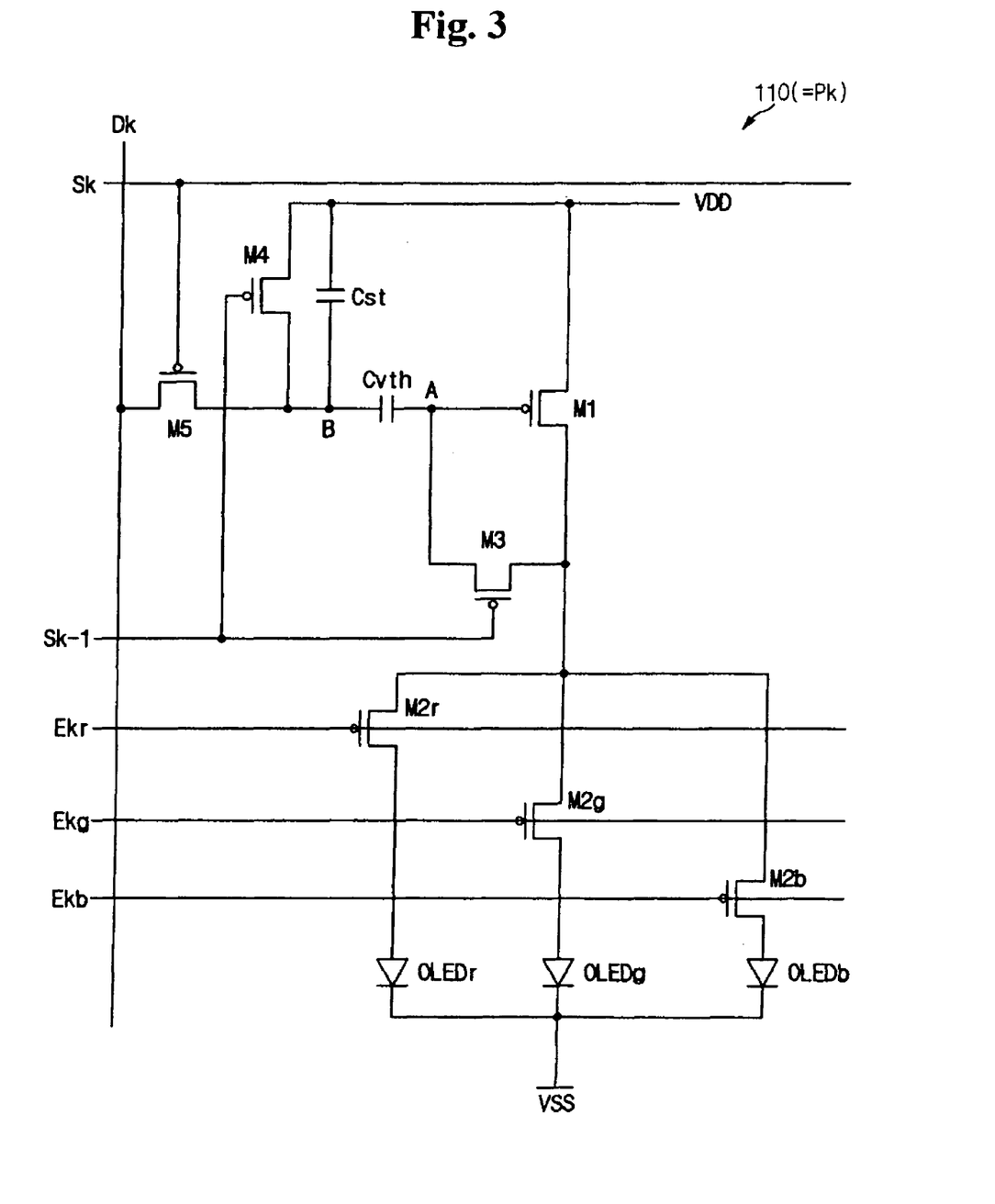
FIG. 3 is an equivalent circuit diagram of a pixel (or a pixel circuit) in the organic EL display of FIG. 2.

FIG. 3 is an equivalent circuit diagram of the pixel 110 in the organic EL display of FIG. 2. The pixel 110 (or Pk) is shown to be coupled to the scan line Sk on the k-th row and the data line on the k-th column, and all the transistors are shown to be p-channel transistors for exemplary purposes. As such, the present invention is not thereby limited.

As shown in FIG. 3, the pixel (or pixel circuit) 110 (or Pk) includes a driving transistor M1, a diode transistor M3, a capacitor transistor M4, a switching transistor M5, three organic light-emitting elements OLEDr, OLEDg and OLEDb, three light emission transistors M2r, M2g and M2b for controlling light emission of the organic light-emitting elements OLEDr, OLEDg and OLEDb, respectively, and two capacitors Cst and Cvth. One light emission control line Ek shown in FIG. 2 includes three light emission control lines Ekr, Ekg and Ekb. The light emission transistors M2r, M2g and M2b selectively transfer a current from the driving transistor M1 to the organic light-emitting elements OLEDr, OLEDg and OLEDb in response to a light emission control signal from the light emission control lines Ekr, Ekg and Ekb.

More specifically, the transistor M5 has a gate coupled to the current scan line Sk, and a source coupled to the data line Dk, and transfers a data voltage from the data line Dk to a node B of the capacitor Cvth in response to the selection signal from the scan line Sk. The transistor M4 couples the node B of the capacitor Cvth directly to a power voltage VDD in response to the selection signal from the previous scan line Sk−1. The transistor M3 is coupled to a node A of the capacitor Cvth and is also coupled to the organic light-emitting elements OLEDr, OLEDg and OLEDb through the transistors M2r, M2g, and M2b, respectively. The transistor M3 diode-connects the transistor M1 in response to the selection signal from the previous scan line Sk−1. The driving transistor M1, which is for driving the organic light-emitting element OLED (e.g., OLEDr, OLEDg and/or OLEDb), has a gate coupled to the node A of the capacitor Cvth, and a source coupled to the power supply voltage VDD, to control a current to be applied to the organic light-emitting element OLED (e.g., OLEDr, OLEDg and/or OLEDb) using the voltage applied to its gate.

Also, one electrode of the capacitor Cst is coupled to the power supply voltage VDD and the other electrode thereof is coupled to a drain electrode of the transistor M4 (e.g., at around the node B). One electrode or node B of the capacitor Cvth is coupled to the other electrode of the capacitor Cst to form a serial connection of the two capacitors Cst and Cvth, and the other electrode thereof is coupled to the gate of the driving transistor M1 (e.g., at around the node A).

The drain of the driving transistor M1 is coupled to the sources of the light emission transistors M2r, M2g and M2b. The gates of the transistors M2r, M2g and M2b are coupled to the light emission control lines Ekr, Ekg and Ekb, respectively. The drains of the light emission transistors M2r, M2g and M2b are coupled to the anodes of the organic light-emitting elements OLEDr, OLEDg and OLEDb, respectively. The cathodes of the organic light-emitting elements OLEDr, OLEDg and OLEDb are coupled to a power supply voltage VSS that is lower than the power supply voltage VDD. The power supply voltage VSS can include a negative voltage, or a ground voltage.

In operation, when a "low" (or a low level) scan voltage is applied to the previous scan line Sk−1, the transistors M3 and M4 are turned on. With the transistor M3 being on, the transistor M1 is diode-connected. Hence, the voltage difference between the gate and the source of the transistor M1 varies until it reaches a threshold voltage Vth of the transistor M1. The source of the transistor M1 is coupled to the power supply voltage VDD, so the voltage applied to the gate of the transistor M1, i.e., the node A of the capacitor Cvth is the sum of the power supply voltage VDD and the threshold voltage Vth. Further, with the transistor M4 being on, the power voltage VDD is applied to the node B of the capacitor Cvth. As such, a voltage $V_{Cvth}$ charged in the capacitor Cvth is given by the following Equation 2.

$$V_{Cvth} = V_{CvthA} - V_{CvthB} = (VDD + Vth) - VDD = Vth \quad \text{[Equation 2]}$$

where $V_{Cvth}$ is the voltage charged in the capacitor Cvth; $V_{CvthA}$ is the voltage applied to the node A of the capacitor Cvth; and $V_{CvthB}$ is the voltage applied to the node B of the capacitor Cvth.

When a "low" scan voltage is applied to the current scan line Sk, the transistor M5 is turned on, and the data voltage Vdata is applied to the node B. The capacitor Cvth is charged with the voltage corresponding to the threshold voltage Vth of the transistor M1. Hence, a voltage corresponding to the sum of the data voltage Vdata and the threshold voltage Vth of the transistor M1 is applied to the gate of the transistor M1. That is, the gate-source voltage Vgs of the transistor M1 is given by the following Equation 3. Here, a "high" (or a high level) signal is applied to the light emission control line Ek (e.g., Ekr, Ekg, and/or Ekb) to turn off the transistor M2 (e.g., M2r, M2g, and/or M2b) to block a current flow.

$$Vgs = (Vdata + Vth) - VDD \quad \text{[Equation 3]}$$

Subsequently, a "low" signal applied to the light emission control line Ek turns on the transistor M2 to supply a current $I_{OLED}$ corresponding to the gate-source voltage Vgs of the transistor M1 to the organic light-emitting element OLED (e.g., OLEDr, OLEDg, and/or OLEDb), causing the organic light-emitting element OLED to emit a light or lights. The current $I_{OLED}$ is given by the following Equation 4.

$$I_{OLED} = \frac{\beta}{2}(Vgs - Vth)^2 \quad \text{[Equation 4]}$$
$$= \frac{\beta}{2}(Vdata + Vth - VDD) - Vth)^2$$
$$= \frac{\beta}{2}(VDD - Vdata)^2$$

where $I_{OLED}$ is the current flowing to the organic light-emitting element OLED; Vgs is the source-gate voltage of the transistor M1; Vth is the threshold voltage of the transistor M1; Vdata is the data voltage; and β is a constant.

In more detail, when the data voltage Vdata is a red data signal, and the transistor M2r is turned on in response to the "low" light emission control signal from the light emission control line Ekr, the current $I_{OLED}$ is applied to the red organic light-emitting element OLEDr, causing the red organic light-emitting element OLEDr to emit a light.

Likewise, when the data voltage Vdata is a green data signal, and the transistor M2g is turned on in response to the "low" light emission control signal from the light emission control line Ekg, the current $I_{OLED}$ is applied to the green organic light-emitting element OLEDg, causing the green organic light-emitting element OLEDg to emit a light. When the data voltage Vdata is a blue data signal, and the transistor M2b is turned on in response to the "low" light emission control signal from the light emission control line Ekb, the current $I_{OLED}$ is applied to the blue organic light-emitting element OLEDb, causing the blue organic light-emitting element OLEDb to emit a light. Here, the three light emission control signals applied to the three respective light emission control lines have a low level interval not overlapping in one field (or not superimposed on one another) so as to represent all the three colors, red, green and blue in one pixel.

Hereinafter, a layout of a pixel area for one pixel circuit in an organic EL display according to the exemplary embodiment of the present invention will be described in further detail with reference to FIGS. 4, 5 and 6. In addition, certain components of the current pixel Pk have normal reference numerals, and certain components of the previous pixel Pk−1 have a symbol "'" that is attached to the same reference numerals to thus distinguish the certain components of the current pixel Pk and the certain components of the previous pixel.

Figure 4:
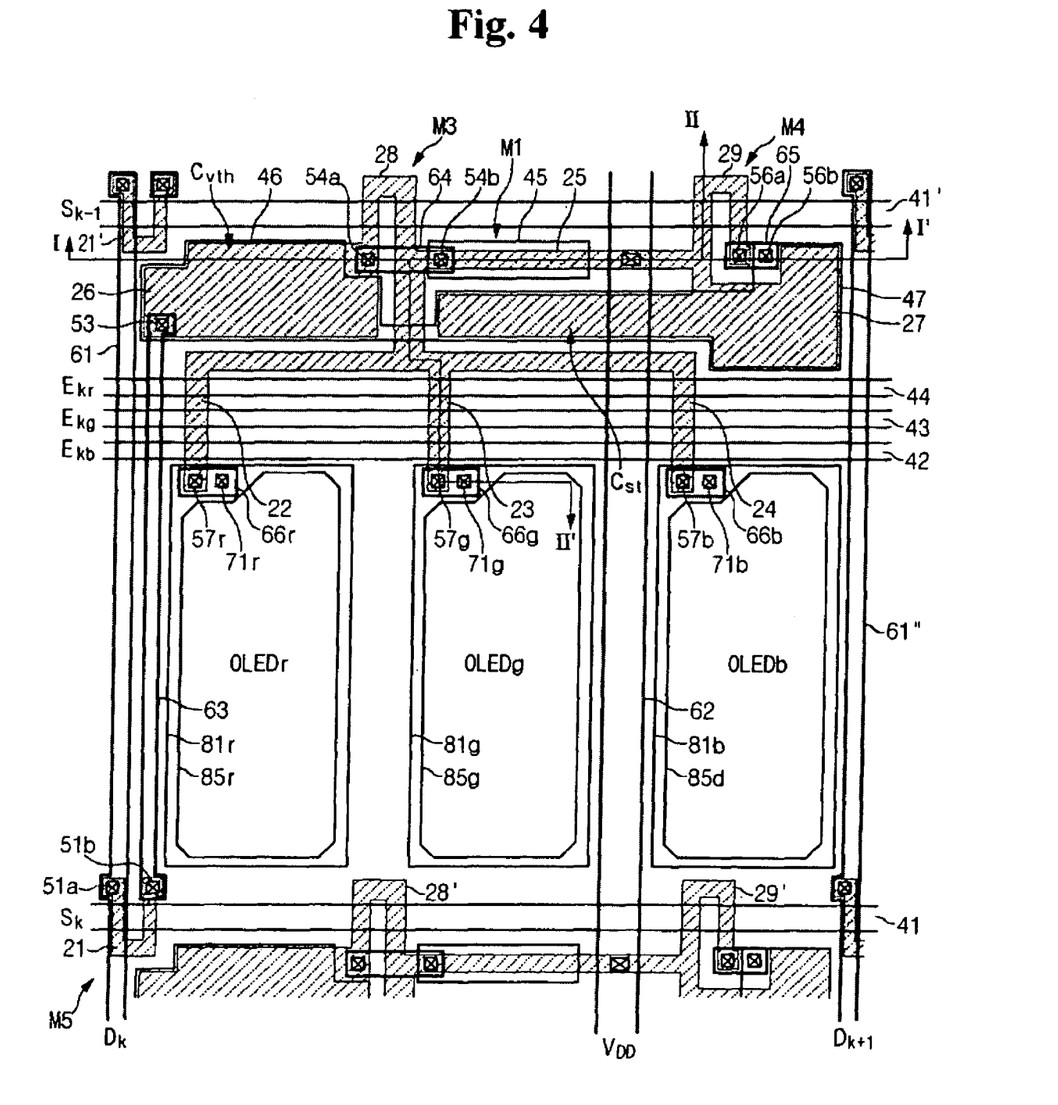
FIG. 4 is a plan view showing an example of a layout of the pixel circuit of FIG. 3.

FIG. 4 is a plan view showing an example of a layout of the pixel circuit shown in FIG. 3. FIG. 5 is a cross-section taken by the line I-I' of FIG. 4 in a row direction, and FIG. 6 is a cross-section taken by the line II-II' of FIG. 4 in a column direction.

Figure 5:
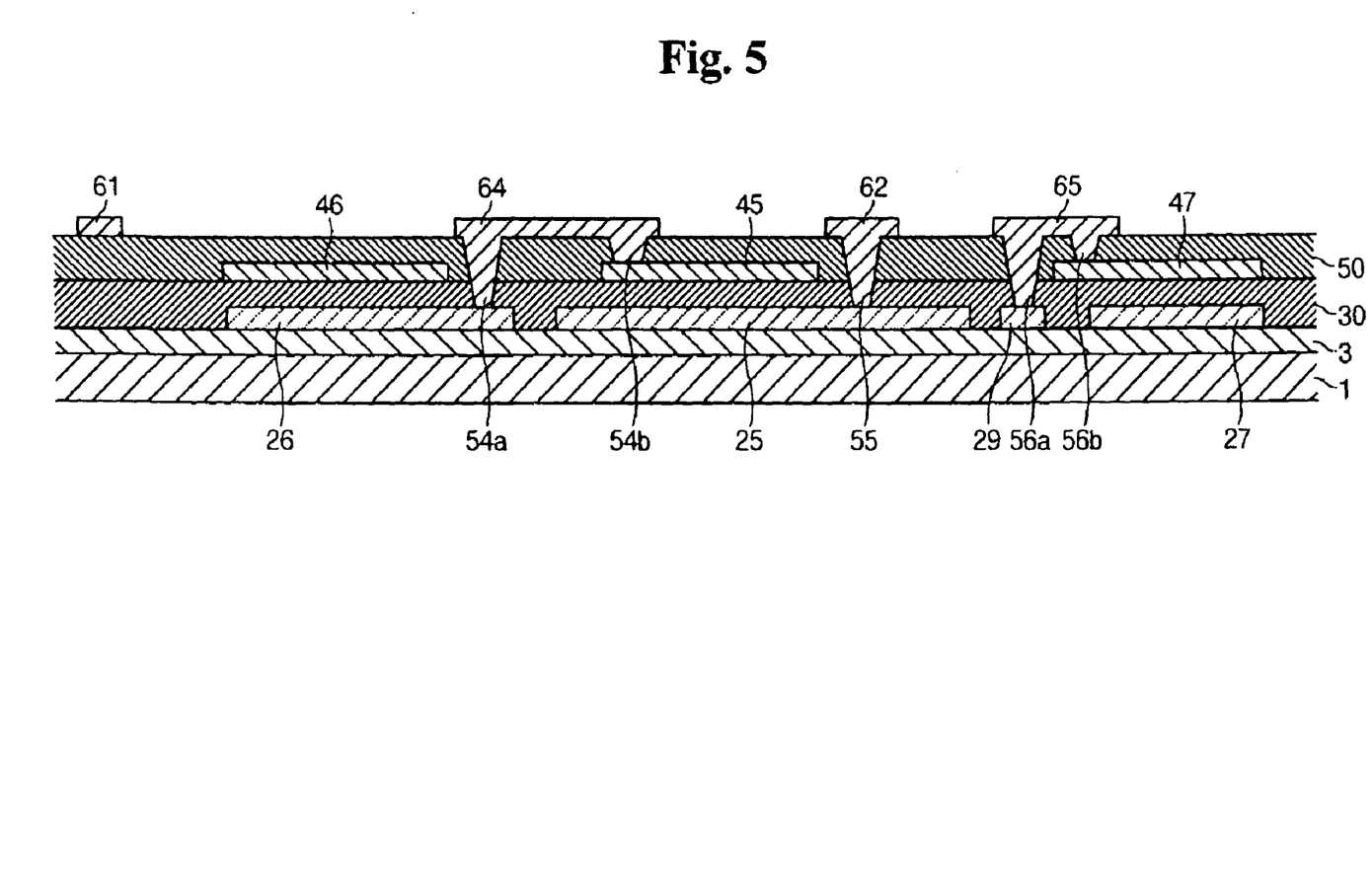
FIG. 5 is a cross-sectional view taken by the line I-I' of FIG. 4 in a row direction.
Figure 6:
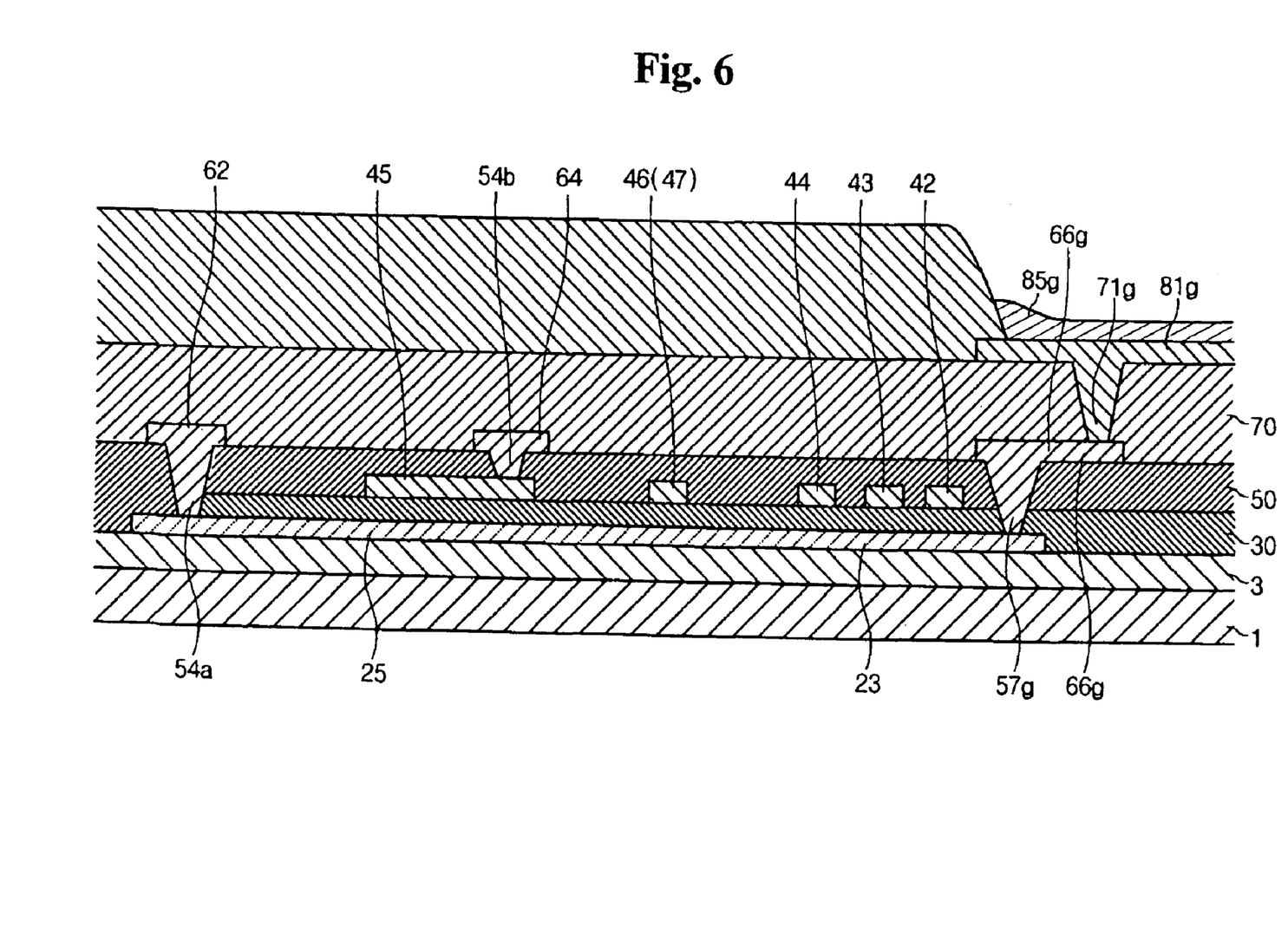
FIG. 6 is a cross-sectional view taken by the line II-II' of FIG. 4 in a column direction.

Referring to FIGS. 4, 5 and 6, a shield layer 3 is formed from silicon oxide on an insulating substrate 1 (shown in FIGS. 5-6), and polysilicon layers 21, 22, 23, 24, 25, 26, 27, 28, and 29, which are semiconductor layers represented by shaded areas, are formed on the shield layer 3.

The polysilicon layer 21 is a 'U'-shaped part in the bottom left corner of FIG. 4 to form a semiconductor layer including source, drain and channel regions of the transistor M5 of the current pixel Pk. The polysilicon layer 22 is an approximately 'ㄱ'-shaped part over the light-emitting element OLEDr to form a semiconductor layer including source, drain and channel regions of the transistor M2r of the current pixel Pk. The polysilicon layer 23 extends in the column direction over the light-emitting element OLEDg to form a semiconductor layer including source, drain and channel regions of the transistor M2g of the current pixel Pk. The polysilicon layer 24 is an approximately 'ㄱ'-shaped part over the light-emitting element OLEDb to form a semiconductor layer including source, drain and channel regions of the transistor M2b of the current pixel Pk. The polysilicon layers 22, 23 and 24 are integrally coupled to one another to form an approximately 'm'-shape. The polysilicon layer 22 is approximately symmetrical to the polysilicon layer 24 about the polysilicon layer 23.

The polysilicon layer 25 extends lengthwise in the row direction in the top center of the pixel area to form a semiconductor layer including source, channel and drain regions of the transistor M1. The polysilicon layer 26 is an approximately rectangular part to form the one electrode (node A) of the capacitor Cvth. The polysilicon layer 27 is an approximately long rectangular part extending in the row direction to form the one electrode of the capacitor Cst. The polysilicon layer 28 is an approximately 'n'-shaped part extending lengthwise in the column direction between the polysilicon layers 26 and 27 to form source, drain and channel regions of the transistor M3. The one end of the polysilicon layer 28 is coupled to the polysilicon layer 26. The other end of the polysilicon layer 28 is coupled to the polysilicon layer 25, and the polysilicon layers 22, 23 and 24. The polysilicon layer 29 is an approximately 'n'-shaped part, with the one end thereof coupled to the polysilicon layer 25 and the polysilicon layer 27, to form source, channel and drain regions of the transistor M4.

A gate insulating layer 30 is formed on the polysilicon layers 21, 22, 23, 24, 25, 26, 27, 28, and 29.

Gate electrode lines 41, 42, 43, 44, 45, 46, and 47 are formed on the gate insulating layer 30 as shown in FIG. 4. More specifically, the gate electrode line 41 extends in the row direction corresponding to the current scan line Sk of the current pixel Pk and insulatively intersects the polysilicon layer 21 to form the gate electrode of the transistor M5 of the current pixel Pk. The gate electrode line 42 extends in the row direction corresponding to the light emission signal line Ekb of the current pixel Pk to form the gate electrode of the transistor M2b. The gate electrode line 43 extends in the row direction corresponding to the light emission signal line Ekg of the current pixel Pk to form the gate electrode of the transistor M2g. The gate electrode line 44 extends in the row direction corresponding to the light emission signal line Ekr of the current pixel Pk to form the gate electrode of the transistor M2r. The gate electrode line 45 is a rectangular part insulatively intersecting the polysilicon layer 25 to form the gate electrode of the transistor M1. The gate electrode line 46 is an approximately rectangular part on the polysilicon layer 26 to form the other electrode (node B) of the capacitor Cvth. The gate electrode line 47 is an approximately rectangular part on the polysilicon layer 27 to form the other electrode (node B) of the capacitor Cst.

The gate electrode line 41' extends in the row direction corresponding to the previous scan line Sk-1 of the previous pixel Pk-1 and insulatively intersects the polysilicon layer 21' to form the gate electrode of the transistor M5 of the previous pixel Pk-1. In addition, the gate electrode line 41' insulatively intersects the polysilicon layers 28 and 29 to form the gate electrodes of the transistors M3 and M4 of the current pixel Pk.

An interlayer insulating layer 50 is formed on the gate electrodes 41, 42, 43, 44, 45, 46, and 47. A surface of the interlayer insulating layer 50 may include a data line 61, a power line 62, and electrodes 63, 64, 65, 66r, 66g and 66b in contact with the corresponding electrodes through contact holes 51a, 51b, 53, 54a, 54b, 55 (shown in FIG. 5), 56a, 56b, 57r, 57g and 57b.

The data line 61, which extends lengthwise in the column direction between the pixel area of FIG. 4 and another pixel area, is coupled to the polysilicon layer 21 through the contact hole 51a piercing the interlayer insulating layer 50 (shown in FIG. 5) and the gate insulating layer 30 (shown in FIG. 5) and to the source of the transistor M4.

The power line 62, which extends lengthwise in the column direction, is coupled to the polysilicon layers 27, 28, and 29 through the contact hole 55 (shown in FIG. 5) piercing the interlayer insulating layer 50 (shown in FIG. 5) and the gate insulating layer 30 (shown in FIG. 5), to supply power to the one electrode of the capacitor Cst and the source of the transistor M1.

The electrode 63 adjoins the data line 61 in parallel and acts as the node B coupling the drain region of the polysilicon layer 21 and the gate electrode 46 through the contact hole 51b piercing the interlayer insulating layer 50 (shown in FIG. 5) and the gate insulating layer 30 (shown in FIG. 5) and the contact hole 53 piercing the interlayer insulating layer 50 (shown in FIG. 5).

The electrode 64 adjoins the gate electrode 41' in parallel and acts as the node A coupling the drain region of the transistor M3 in the polysilicon layer 28 and the gate electrode 45 through the contact hole 54a piercing the interlayer insulating layer 50 (shown in FIG. 5) and the gate insulating layer 30 (shown in FIG. 5) and the contact hole 54b piercing the interlayer insulating layer 50 (shown in FIG. 5).

The electrode 65 adjoins the gate electrode 41' in an approximately rectangular form and acts as the node B coupling the drain region of the transistor M4 in the polysilicon layer 29 and the gate electrode 47 through the contact hole 56a piercing the interlayer insulating layer 50 (shown in FIG. 5) and the gate insulating layer 30 and the contact hole 56b piercing the interlayer insulating layer 50 (shown in FIG. 5).

As shown in FIG. 4, the electrodes 66r, 66g and 66b are used to couple pixel electrodes 81r, 81g and 81b of each light-emitting element and the drains of the transistors M2r, M2g and M2b (shown in FIG. 2), respectively. The electrodes 66r, 66g and 66b lie in an approximately rectangular form of which the side in the row direction along the gate electrodes 42, 43, and 44 is longer than the side in the column direction along the data line 62. The electrodes 66r, 66g and 66b are coupled to the drain electrodes of the transistors M2r, M2g and M2b in contact with the polysilicon layers 22, 23 and 24 through the contact holes 57r, 57g and 57b piercing the gate insulating layer 30 (shown in FIG. 5) and the interlayer insulating layer 50 (shown in FIG. 5), respectively.

FIG. 6 depicts a cross-sectional view of a green pixel for exemplary purposes. The following description may also be extended to the red pixel and the blue pixel. A planarizing layer 70 is formed on the electrode 66g. The planarizing layer may also be formed on electrodes 63, 64, 65, 66r, and 66b (shown in FIG. 4). The pixel electrodes 81r, 81g and 81b are coupled to the electrodes 66r, 66g and 66b through the contact holes 71r, 71g and 71b piercing the planarizing layer 70, respectively. As illustrated in FIG. 6 (and/or FIG. 4), red, green and blue organic thin films 85r (shown in FIG. 4), 85g and 85b (shown in FIG. 4) of an interlayer structure including a light-emitting layer (EML), an electron transport layer (ETL) and a hole transport layer (HTL) are formed on the pixel electrodes 81r, 81g and 81b, respectively.

As illustrated in FIG. 4, in an embodiment the scan line 41 extends from the data line 61 and insulatively intersects the polysilicon layers 21, 28' and 29' in sequence, to form the switching transistor M5 of the current pixel Pk, and the transistors M3 and M4 of the next pixel Pk+1. Likewise, the scan line 41' extends from the data line 61 and insulatively intersects the polysilicon layers 21', 28 and 29 in sequence, to form the switching transistor M5 of the previous pixel Pk−1, and the transistors M3 and M4 of the current pixel Pk.

In more detail, the switching transistor M5 is formed adjacent to the data line 61, so the electrode line 63 coupling the source of the switching transistor M5 and the one electrode (or the node B) of the capacitor Cvth can adjoin the data line 61 in parallel. In addition, the transistor M4 is formed apart from the data line 61 in the pixel area (and adjacent to a second data line 61"), so the source of the transistor M4 can be arranged adjacent to the power line 62. The transistor M3 can be arranged between the transistors M5 and M4. As such, the switching transistor M5 of the previous pixel and the transistors M3 and M4 of the current pixel are sequentially arranged from the data line, so the elements in the pixel area can be arranged efficiently.

The exemplary embodiment of the present invention has been described by a pixel circuit which includes five transistors, two capacitors, and three emit elements; however, the present invention is not thereby limited. Embodiments of the present invention can be applicable to a pixel circuit having one emit element, two emit elements, four emit elements, and/or more than four emit elements and can also be applicable to a pixel circuit with one, two, and/or more transistors, and/or one or more capacitors (e.g., the two transistors and one capacitor embodiment of FIG. 1).

In general and according to certain embodiments of the present invention, the transistors of which the control electrodes are coupled to the scan line between two adjacent data lines are arranged in the order of the switching transistor (e.g., the switching transistor M5) of the previous pixel and the transistors (e.g., the transistors M3 and M4) of the current pixel, so as to achieve a more efficient arrangement of elements in the pixel area.

In addition, a power electrode line (e.g., the power line 62) can be provided between two transistors (e.g., transistors M3 and M4), so it can be arranged adjacent to the source electrode of one of the two transistors (e.g., the transistor M4).

While the invention has been described in connection with certain exemplary embodiments, it is to be understood by those skilled in the art that the invention is not limited to the disclosed embodiments, but, on the contrary, is intended to cover various modifications included within the spirit and scope of the appended claims and equivalents thereof.

What is claimed is:

1. A display panel comprising:
   a scan line having at least an extending area extending lengthwise in a first direction;
   first, second and third semiconductor layer areas insulatively intersecting the extending area of the scan line; and
   a data electrode extending in a second direction, and being coupled to the one end of the first semiconductor layer area through a contact hole,
   the second semiconductor layer area being arranged between the first semiconductor layer area and the third semiconductor layer area.

2. The display panel as claimed in claim 1, wherein each of the first, second and third semiconductor layer areas intersects the scan line at least twice.

3. The display panel as claimed in claim 2, wherein the first semiconductor layer area is formed in an approximate "U" shape.

4. The display panel as claimed in claim 3, wherein the second and third semiconductor layer areas are formed in an approximate "n" shape.

5. The display panel as claimed in claim 1, further comprising a second data electrode adjacent to said data electrode and extending in the second direction, wherein the first, second and third semiconductor layer areas cross a portion of the extending area of the scan line between said data electrode and the second data electrode.

* * * * *